United States Patent [19]
Bacskai

[11] 3,992,430

[45] Nov. 16, 1976

[54] PROCESS FOR PREPARING AROMATIC ISOCYANATES

[75] Inventor: Robert Bacskai, Kensington, Calif.

[73] Assignee: Chevron Research Company, San Francisco, Calif.

[22] Filed: Sept. 11, 1975

[21] Appl. No.: 612,408

[52] U.S. Cl. .......................... 260/453 P; 260/471 C
[51] Int. Cl.² ....................................... C07C 118/00
[58] Field of Search ................ 260/471 C, 453 P

[56] References Cited
UNITED STATES PATENTS 3,734,941    5/1973    Sydor ............................. 260/453 P

OTHER PUBLICATIONS

Volodavskaya et al.; Chemical Abstracts, vol. 74, p. 99208m (1971).

*Primary Examiner*—Lewis Gotts
*Assistant Examiner*—Dolph H. Torrence
*Attorney, Agent, or Firm*—G. F. Magdeburger; John Stoner, Jr.; W. Keith Turner

[57] ABSTRACT

A process for preparing aromatic isocyanates from aryl-subsituted urethanes by transesterifying a urethane with a phenolic compound to form an N-aryl arylcarbamate, and thermally decomposing the N-aryl arylcarbamate to form the aromatic isocyanate.

4 Claims, No Drawings

PROCESS FOR PREPARING AROMATIC ISOCYANATES

BACKGROUND OF THE INVENTION

This invention relates to the preparation of aromatic isocyanates from aromatic urethanes by phenolic transesterification and thermal decomposition.

Organic isocyanates are useful intermediates in the preparation of urethane foams, coatings and fibers, as well as in the preparation of various phytotoxic and insecticidal agents. Aromatic isocyanates, such as toluene diisocyanate, are particularly useful and have gained widespread industrial recognition.

Heretofore, aromatic isocyanates have generally been prepared by the reaction of an amine in an inert solvent with phosgene. For example, U.S. Pat. No. 2,311,046, granted Feb. 16, 1943, describes the manufacture of aromatic isocyanates by reacting an aromatic amine with phosgene; and U.S. Pat. No. 2,689,861, granted Sept. 21, 1954, describes the manufacture of aromatic isocyanate by reacting an amine with phosgene in the presence of tetramethyl urea. Such processes, while satisfactory, do not proceed as straightforwardly as appears. The isocyanate which is formed may react with the starting amine to form substituted ureas, thus decreasing the yield of desired product. U.S. Pat. No. 2,683,160, granted July 6, 1954, discloses a variety of proposed improvements in the phosgenation process. However, even these improved processes are disadvantageous in many respects, principally in the use of phosgene and the production of acid by-products.

Methods have been proposed which eliminate the use of phosgene, but none have found commercial acceptance due to the cost of materials, unusual reaction conditions, poor yields, or unpredictable side reactions. Phosgene-free processes, in general, have involved the catalytic reaction of an organic nitro compound and carbon monoxide. U.S. Pats. Nos. 3,728,370, granted Apr. 17, 1973; 3,743,664, granted July 3, 1973; 3,600,419, granted Aug. 17, 1971; 3,632,827, granted Jan. 4, 1972; 3,597,466, granted Aug. 3, 1971, 3,585,231, granted June 15, 1971, 3,576,836, granted Apr. 27, 1971; 3,576,835, granted Apr. 27, 1971; 3,523,963, granted Aug. 11, 1970; 3,523,964, granted Aug. 11,1970; and 3,523,965, granted Aug. 11, 1970, disclose various noble metal-catalyzed reactions of aromatic nitro compounds with carbon monoxide to form an aromatic isocyanate.

Recent interest has been focused on the non-catalytic pyrolysis of urethanes to prepare isocyanates. For example, U.S. Pat. No. 3,734,941, granted May 22, 1973, granted May 22, 1973, describes the pyrolysis of urethane at a temperature of 400° to 600° C to prepare the corresponding isocyanate. Similarly, U.S. Pat. No. 3,870,739 describes the pyrolysis of urethanes at a temperature of 350° to 550° C under conditions of controlled residence time and pressure to form an isocyanate.

The harsh reaction conditions required and relatively low yield obtained by current phosgene-free isocyanate syntheses make it desirable to provide a synthetic route to aromatic isocyanates which does not employ phosgene, expensive reactants or catalysts, or harsh reaction conditions.

SUMMARY OF THE INVENTION

It has been found that urethanes can be transesterified with a phenolic compound to form an N-aryl arylcarbamate which can be readily decomposed at a temperature below about 300° C to yield the corresponding aromatic isocyanate.

DETAILED DESCRIPTION OF THE INVENTION

The present invention provides a process for preparing aromatic isocyanates which comprises transesterifying an N-aryl alkylcarbamate with a phenolic compound to form an N-aryl arylcarbamate, and thermally decomposing the N-aryl arylcarbamate at a temperature from about 200° to about 300° C, preferably about 250° C, to form an aromatic isocyanate.

In detail, any N-aryl alkylcarbamate capable of being converted to an N-aryl arylcarbamate be esterification with a phenolic compound may be employed as a starting material. Typical suitable N-aryl alkylcarbamates include urethanes having the formula.

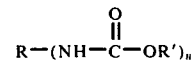

wherein R is aryl, R' is straight- or branched-chain alkyl, containing from 1 to about 16 carbon atoms, preferably from 1 to 2 carbon atoms, carbon atoms, and $n$ is 1 or 2. Accordingly, representative N-aryl alkylcarbamates suitable for use herein include, for example:

N-phenyl propylcarbamate;
N-p-cumenyl hexylcarbamate;
N-mesityl-(3-methyl heptylcarbamate);
N-xylyl hexylcarbamates;
N-o-tolyl butylcarbamate;
N-m-tolyl isobutylcarbamate;
N-phenyl neopentylcarbamate;
N-phenyl dodecylcarbamate;
N-phenyl hexadecylcarbamate;
N-cymyl octylcarbamates;
N-naphthyl methylcarbamates;
N-anthracyl ethylcarbamates;
N-p-tolyl propylcarbamate;
N,N'-toluene-2,4- di(methylcarbamate);
N-(p-methoxycarbonylaminophenyl)urethane;
p,p'-biphenyl di(methylcarbamate);
bis(p-methoxycarbonylaminophenyl)urethane; and the like.

Preferred N-aryl alkyl carbamates include, for example, N-(p-methoxycarbonylaminophenyl)urethane; p,p'-biphenyl di(methylcarbamate); bis(p-methoxycarbonylaminophenyl)urethane; and the like.

In general, urethanes are prepared by the catalytic reaction of a nitro-aromatic compound with carbon monoxide in an alcohol solvent, as thoroughly described in British Pat. No. 993,704, published June 2, 1965, incorporated herein by reference.

In addition, isomers and mixtures of the aforesaid urethanes may also be employed, as well as the substituted N-aryl alkylcarbamates, homologs and related compounds. 2,4-toluene di(methylcarbamate) is especially preferred for use in the practice of this invention.

It has been found that N-aryl alkylcarbamates may be successfully transesterified in the presence of a phenoiic compound. Phenolic compounds which may be employed in the transesterification of the N-aryl alkylcarbamates may be substituted or unsubstituted and include, for example, phenols, cresols, alkylphenols and xylenols. A thorough description of suitable phenolic compounds having a hydroxy substituent directly attached to an aromatic nucleus can be found in "Chemistry of Organic Compound," Noller (Ed.) 1966, at pages 550 et seq. In general, those phenolic compounds or mixtures thereof which will exchange an aryl substituent for the alkyl substituent of an N-aryl alkylcarbamate are suitable for use in the practice of this invention.

The transesterification reaction proceeds according to the reaction scheme:

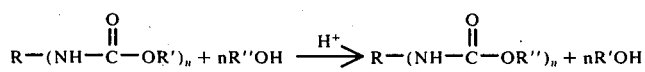

wherein R and R'' are aryl, R' is alkyl, and $n$ is an integer from 1 to 2. The reaction may be carried out at typical transesterification temperatures from about 4° to 300° C, preferably from 80° to 220° C, and atmospheric pressure in a solvent medium with the aid of an acid catalyst. Removal of R'OH by-product by distillation during reaction improves the yield of arylcarbamate.

Any of the various catalyst and solvent systems typical of transesterification reactions are suitable for use in the practice of this invention. For example, suitable solvents include toluene, resorcinol, dodecylphenol, phenol, and the like; and suitable acid catalysts include, for example, paratoluene sulfonic acid, sulfuric acid, phosphoric acid, hydrochloric acid, and the like.

Following transesterification, the reaction products can be separated by conventional techniques such as vacuum distillation. The recovered N-aryl arylcarbamates can be thermally decomposed under relatively mild pyrolytic conditions to yield an aromatic isocyanate. Decomposition proceeds according to the reaction scheme:

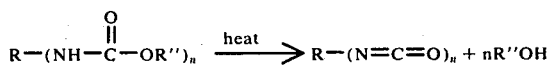

wherein R, R'' and $n$ are as defined above. The pyrolytic decomposition may be carried out at a temperature of from about 200° to about 300° C, preferably about 250° C, at atmospheric pressure. Temperatures in excess of about 300° C are undesirable from the standpoint of product yield and purity, as well as energy consumption and process control. Temperatures below about 200° C are not sufficient to effect decomposition. While atmospheric pressures are satisfactory, subatmospheric pressures may be used to facilitate product separation and to promote the decomposition at low temperatures. Particularly good results are achieved when pressures from about 1 to about 300 psig are employed with temperatures from about 200 to about 300° C. Product separation can be carried out using conventional procedures such as distillation and condensation.

EXAMPLE

The following example further illustrates the practice of this invention.

EXAMPLE 1

Preparation of Toluene Diisocyanate

A 200 ml flask equipped with a short distillation adapter was charged with 50 g of p-cresol, 21.1 g of toluene and 0.5 of p-toluene sulfonic acid. The flask was heated and 5.3 ml of toluene were distilled off. After cooling, 5.3 ml of toluene and 10 g (.042 mols) of N,N'-toluene-2,4-di(methylcarbamate) were charged to the flask. This flask was then attached to a "Todd" distillation apparatus. Transesterification was carried out at a pot temperature of 163°–198° C with azeotropic distillation of byproduct methanol. Overhead fractions (b.p. 105° to 108° C) of 10 ml each were taken. Each time 10 ml of distillate was removed an additional 10 ml of toluene was added to the flask. Analysis of the overhead fractions by VPC showed decreasing amounts of methanol, until there was none in fraction 5. Aliquots of the bottoms were analyzed by infrared. Initial analysis showed absorption at 1708 cm$^{-1}$ (N,N'-toluene-2,4-di(methylcarbamate)), but as the reaction proceeded, the 1708 cm$^{-1}$ peak disappeared and was replaced by absorption at 1720 cm$^{-1}$ (N,N'-toluene-2,4-di(p-cresylcarbamate).

Analysis of the crude reaction product by VPC at an injection port temperature of 250° C and a column temperature of 220° C, gave 0.0249 mols of toluene diisocyanate, a 59.3% yield based on the dimethylcarbamate feedstock. Distillation of the crude reaction mixture at 110°–123° C/31 mm produced 8.6 g of a mixture containing the toluene diisocyanate.

What is claimed is:

1. A process for preparing aromatic isocyanates, which comprises: transesterifying an N-aryl alkylcarbamate with a phenolic compound having a hydroxy group directly attached to an aromatic nucleus to prepare an N-aryl arylcarbamate; and thermally decomposing said N-aryl arylcarbamate at a temperature from about 200° to 300° C to prepare said aromatic isocyanate.

2. A process according to claim 1, wherein said N-aryl alkylcarbamate is 2,4-toluene di(methylcarbamate).

3. A process according to claim 2 wherein said phenolic compound is para-cresol.

4. A process according to claim 1 wherein said thermal decomposition is carried out at a temperature of about 250° C.

* * * * *